United States Patent [19]

Ryan et al.

[11] 4,115,374

[45] Sep. 19, 1978

[54] SUBSTRATES FOR ANGIOTENSIN CONVERTING ENZYME

[76] Inventors: James Walter Ryan, 3420 Pionciana Ave., Miami, Fla. 33133; Alfred Chung, 8781 SW 87th St., Miami, Fla. 33173

[21] Appl. No.: 795,497

[22] Filed: May 10, 1977

[51] Int. Cl.² .......................................... C07C 103/52
[52] U.S. Cl. ....................... 260/112.5 R; 195/103.5 R
[58] Field of Search ................................. 260/112.5 R

[56] References Cited

U.S. PATENT DOCUMENTS 4,057,629  11/1977  Miki et al. .................... 260/112.5 R

*Primary Examiner*—Delbert R. Phillips
*Attorney, Agent, or Firm*—Lorance L. Greenlee

[57] ABSTRACT

The novel compounds Iodo-p-hydroxyphenyl-glycyl-glycylglycine and Benzoylprolylphenylalanylarginine are disclosed, together with radioisotope labeled forms thereof, wherein the radioisotope is incorporated in the Iodo-p-hydroxyphenyl moiety or the Benzoyl moiety, respectively. These compounds are useful as substrates for angiotensin converting enzyme in an assay for that enzyme's activity.

6 Claims, 1 Drawing Figure

SUBSTRATES FOR ANGIOTENSIN CONVERTING ENZYME

BACKGROUND

Angiotensin converting enzyme (peptidyl dipeptide hydrolase, hereinafter referred to as ACE) occupies a central role in the physiology of hypertension. The enzyme is capable of converting the decapeptide angiotensin I, having the sequence AspArgValTyrIleHisProPheHisLeu to an octapeptide, angiotensin II by removal of the carboxyterminal HisLeu. The symbols for various chemical entities are explained in the following table:

TABLE I

| | | |
|---|---|---|
| Ala | = | L-alanine |
| Arg | = | L-arginine |
| Asp | = | L-aspartic acid |
| Gln | = | L-glutamine |
| <Glu | = | pyro-L-glutamic acid |
| Gly | = | glycine |
| Hip | = | Hippuric acid (Benzoyl glycine) |
| His | = | L-histidine |
| Ile | = | L-isoleucine |
| Leu | = | L-leucine |
| Lys | = | L-lysine |
| Phe | = | L-phenylalanine |
| Pro | = | L-proline |
| Ser | = | L-serine |
| Trp | = | L-tryptophan |
| Tyr | = | L-tyrosine |
| Val | = | L-valine |
| ACE | = | Angiotensin converting enzyme |
| Bicine | = | N,N-bis (2-hydroxyethyl) glycine |
| EDTA | = | Ethylene diamine tetraacetic acid |
| Hepes | = | N-2-hydroxyethlpiperazine-N'-2-ethanesulfonic acid |
| HPP | = | p-hydroxyphenylpropionyl |

Angiotensin I is formed by the action of the enzyme renin, an endopeptidase found in kidney, other tissues and plasma, acting on renin substrate, a serum $\alpha_2$ globulin.

Blood pressure is affected by certain peptides found in the blood. One of these, angiotensin II, is a powerful pressor (blood pressure elevating) agent. Another, bradykinin, a nonapeptide with the sequence ArgProProGlyPheSerProPhe Arg is a powerful depressor (blood pressure lowering) agent. In addition to a direct pressor effect, angiotensin II stimulates release of aldosterone which tends to elevate blood pressure by causing retention of extracellular salt and fluids. Angiotensin II is found in measurable amount in the blood of normal humans. However, it is found at elevated concentration in the blood of patients with renal hypertension.

The level of ACE activity is ordinarily in excess, in both normal and hypertensive humans, of the amount needed to maintain observed levels of angiotensin II. However, it has been found that significant blood pressure lowering is achieved in hypertensive patients by treatment with ACE inhibitors. (Gavras, H., Brunner, H.R., Laragh, J.H., Sealey, J.E., Gavras, I., and Vukovich, R.A., *New Engl. J. Med* 291, 817 (1974). The ability to measure variations in the ACE activity in patients under treatment with an ACE inhibitor is therefore of great clinical and research importance. In addition, elevated levels of ACE activity have been found to exist in cases of sarcoidosis and also in Gaucher's disease. In some cases of sarcoidosis, ACE levels may be more than two standard deviations above the normal mean. In Gaucher's disease, levels of enzyme activity may be 60 times higher than those of normals. The elevated blood level seen in active sarcoidosis may fall to the normal range when the disease undergoes spontaneous remission or when therapeutic benefit is achieved through treatment. An effective, simple and convenient assay for the activity of ACE in a serum sample is accordingly a highly desirable tool of great utility to the physician who must deal with this disease, which is not only difficult to diagnose but to monitor.

ACE is a peptidyldipeptide hydrolase. It catalyzes the hydrolysis of the penultimate peptide bond at the C-terminal end of a variety of acylated tripeptides and larger polypeptides having an unblocked carboxyl group. The peptide hydrolysis is represented diagrammatically as: $R-A_2-A_1 + H_2O \rightarrow R-OH + H-A_2-A_1$, wherein $A_1$ is an amino acid at the carboxyl terminus of the peptide, $A_2$ is an amino acid linked to $A_1$ by a peptide bond, R is an N-substituted amino acid linked to $A_2$ by a peptide bond. The action of ACE results in hydrolytic cleavage of the penultimate peptide bond from the carboxyl-terminal end yielding as reaction products a dipeptide, $HA_2A_1$, and a remnant, $R-OH$.

The reactivity of the enzyme varies markedly depending on the substrate. At least one type of peptide bond, having the nitrogen supplied by proline, is not hydrolyzed at all. The apparent Michaelis constant (Km) varies from substrate to substrate over several orders of magnitude. For general discussion of the kinetic parameters of enzyme catalyzed reactions, see Lehninger, A., *Biochemistry, Worth Publishers, Inc., New York*, 1970, pp. 153-157. Many peptides which are called inhibitors of the enzymatic conversion of angiotensin I to angiotensin II are in fact substrates having a lower Km than angiotensin I. Such peptides are more properly termed competitive substrates. Examples of competitive substrates include bradykinin, and the peptide BPP$_5\alpha$ (also called SQ20475) from snake venom, whose sequence is <GluLysTrpAlaPro.

ACE requires chloride ions for activity with some but not all substrates and is inhibited by divalent cation binding agents such as EDTA. Such inhibition is due to binding of $Zn^{++}$ at the active site of the enzyme.

For background references see: White, A., Handler, P., and Smith, Ed, *Principles of Biochemistry*, 5th ed., 1973, McGraw-Hill, New York, pp. 589-590, 939-940; Bakhle, Y.S., in *Handbook of Experimental Pharmacology; I. H. page and F. M. Bumpus, eds., vol.* 37, pp. 41-80, Springer Verlag, Berlin, 1974. Soffer, R., *Ann. Rev. Biochem.* 45, 73 (1976); Ondetti, M.A., et al., U.S. Pat. No. 3,832,337, patented Aug. 27, 1974. Erdos, E. G., *Am. J. Med.* 60, (6), 749 (1976).

DESCRIPTION OF THE PRIOR ART

Angiotensin converting enzyme (ACE) activity has been measured by bioassay, radioactivity counting, spectrophotometry and fluorimetry. Methods may be classified according to whether the dipeptide reaction product or the remnant reaction product is measured. In either case, the reaction product to be measured must either be separated from the reaction mixture or treated with a reagent specific for the reaction product.

Among the methods described, based upon measurement of the dipeptide reaction product, the following are noteworthy:

(a) Angiotensin I labeled with $^{14}C$ or $^3H$ in the carboxyterminal leucine moiety was used as substrate. Separation of the dipeptide product was accomplished by gel filtration or ion exchange chromatography. Ryan, J. W., Stewart, J. M., Leary, W. P., and Ledingham, J. G., *Biochem. J.* 120, 221 (1970). Soffer, R. L. Reza, R., an Caldwell, P.R.B., *Proc.Nat.Acad.Sci. USA* 71, 1720 (1974).

(b) The acylated tripeptide HipHisLeu was used as substrate. The dipeptide product HisLeu was measured fluorimetrically following addition of a reagent, o-phthaldialdehyde. The reagent could be used to measure the reaction product in serum without prior separation provided a suitable excess of reagent was added sufficient to form a precipitate with proteins in serum. The fluorescence intensity as a function of HisLeu concentration was nonlinear, therefore, a standard curve was required to calculate the result. Friedland, J., and Silverstein, E., *Am.J.Clin.Path.* 66, 416 (1976). See also, Piquilloud, Y., Reinharz, A., and Roth, M. R., *Biochim.Biophys.Acta* 206, 136 (1970); Depierre, D., and Roth, M., *Enzyme* 19 65 (1975).

(c) The acylated tripeptide HipGlyGly has been employed as substrate in an assay in which the dipeptide reaction product was measured by the ninhydrin reaction. The reaction product was as sayed automatically using an automatic analyzer. Dorer, F. E., Kahn, J. R., Lentz, K. E., Levine, M., and Skeggs, L. T., *Biochim.Biophys.Acta.* 429, 220 (1976) (hereinafter referred to as Dorer, et al.).

In the principal method in which the remnant product was measured, HipHisLeu was used as substrate. The remnant reaction product, hippuric acid was measured spectrophotometrically. The product was first extracted from serum with ethyl acetate. However, in order to measure the product in the spectrophotometer is was necessary to evaporate the ethyl acetate to dryness, then redissolve the hippuric acid quantitatively in an aqueous medium. It was necessary to remove all traces of ethyl acetate prior to measurement. Cushman, D. W., and Cheung, H. S., *Biochem.Pharmac.* 20, 1637 (1971).

A semiquantitative assay using angiotensin I labelled with $^{14}C$ in the phenylalanine moiety was used to determine the fate of angiotensin I upon passage through the vascular bed of intact lung. Separation and identification of the labelled octapeptide reaction product was accomplished by gel filtration, paper electrophoresis and thin layer chromatography. Ryan, J. W., Niemeyer, R. E., Goodwin, D. W., Smith, U., and Stewart, J. M., *Biochem.J.* 125, 921 (1971).

SUMMARY OF THE INVENTION

The present invention provides novel substrates for angiotensin converting enzyme (ACE) which make it possible for the first time to assay the enzyme by measuring the radioactivity of the remnant product resulting from enzymatic hydrolysis of the penultimate peptide bond at the carboxy terminal end of the peptide substrate. These substrates are so designed that the remnant product is extracted nearly quantitatively from serum by an aprotic organic solvent while the nonhydrolyzed substrate is extracted only slightly, if at all. The described substrates and method of assay employing them are designed for use in clinical and research laboratories. Such assays can be carried out on unfractionated biological materials containing ACE, such as serum. They are sensitive, quantitative, easy to carry out and reproducible.

In the assay procedure, samples of biological material in which the ACE content is to be measured are diluted into a reaction buffer providing optimal ionic and pH conditions for the particular substrate employed. Radioactive substrate having a previously measured specific activity is added to the mixture which is then incubated for an appropriate time and temperature. The reaction is then stopped by the addition of a suitable inhibitor and the reaction mixture is extracted with a measured volume of aprotic organic solvent. An aliquot of the solvent, which contains any radioactive remnant reaction product product by action of the enzyme, is transferred directly to a scintillation vial for measurement of radioactivity. The enzyme activity can be calculated from a knowledge of the total radioactivity and amount of substrate in the sample, the amount of radioactivity in the organic solvent aliquot and the time of incubation, after making appropriate corrections for the radioactive counting efficiency, background counts including counts attributable to any hydrolyzed substrate extracted by the solvent, and aliquot size. The result may be expressed in nanomoles of substrate hydrolyzed per minute per milliliter of biological material.

The substrates of the present invention include peptides wherein the labelled remnant contains carbon-14 or tritium, isotopes emitting beta radiation, and peptides labelled with iodine-125, a gamma emitting isotope. Measurement of radioactivity may therefore be carried out with virtually any type of counting equipment having a fixed geometry, suitable for quantitative counting.

The manipulations involved in sample preparation and workup are easily carried out. Where a one hour incubation time is used, results may be obtained in a total of 1.5 hours. The method is able to measure as little as 8 units of enzyme per ml using the assay condition of Example 1, with $^3$H-HipGlyGly as substrate. Greater sensitivity can be achieved by resort to longer incubation time or the use of a substrate such as $^3$H-Benzoyl-ProPheArg, having a lower Km. The term "enzyme unit" as used herein means the amount of activity catalyzing the conversion of one nanomole of substrate per minute per ml. Its significance is further rendered apparent by the fact that normal human serum contains about 85 units – 120 units per ml, using HipGlyGly as substrate.

Advantages of the present method include: simplification of the procedure, reduction of the time required to carry out the assay, elimination of tedious and time consuming separation steps, lack of dependence upon subsequent reactions with reagent, lack of interference by other materials present in the assay mixture, improved recovery due to a reduction of fluid transfer steps, high sensitivity provided by the use of radioisotope measurements and straightforward quantitation without resorting to standard curves for interpretation of results.

DETAILED DESCRIPTION OF THE INVENTION AND PREFERRED EMBODIMENTS

Figure 1:
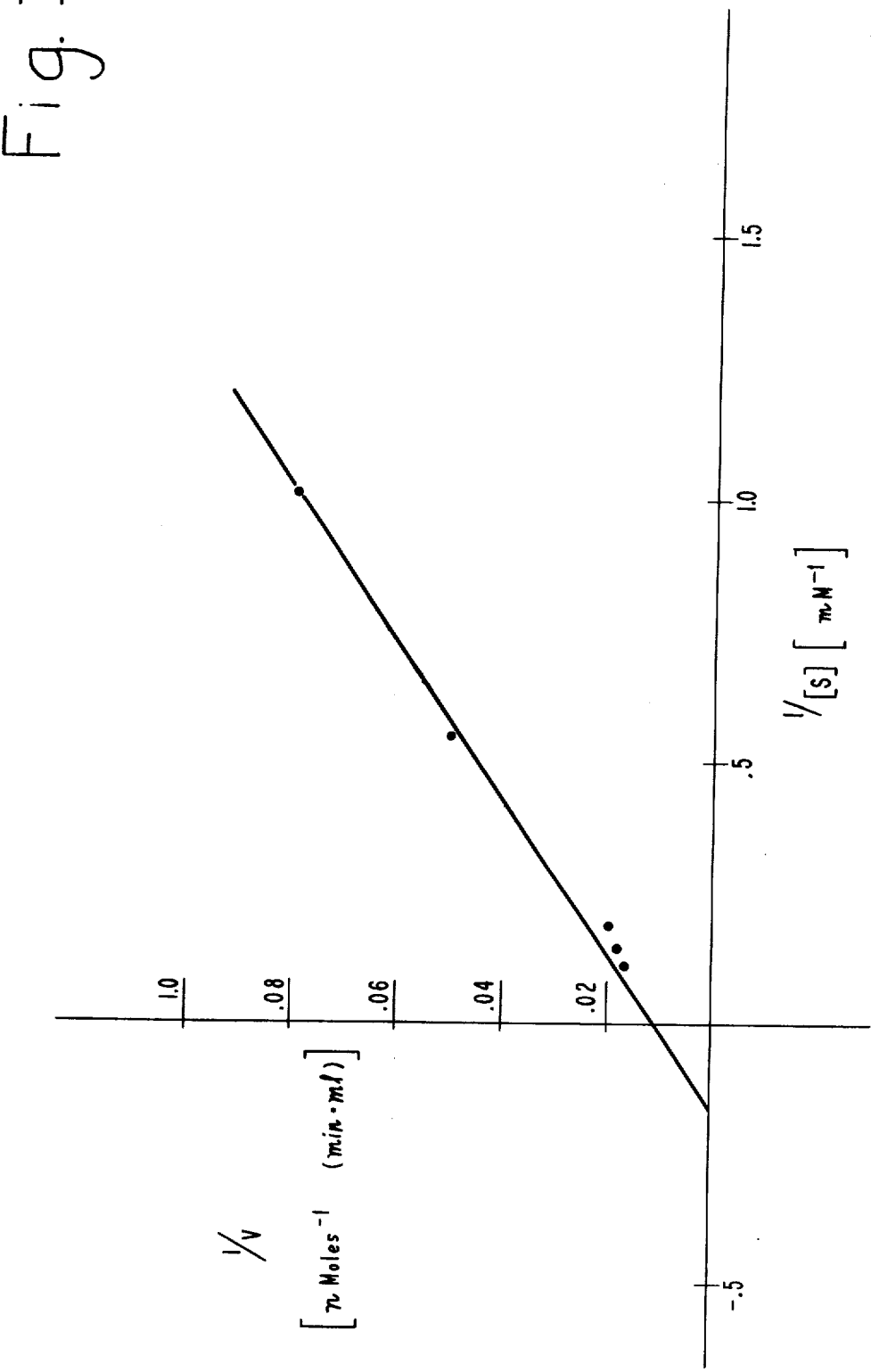

The substrates of the present invention have the property of being separable from their ACE catalyzed hydrolysis products by extraction with an aprotic organic solvent. In the preferred embodiment, the substrate is largely insoluble in the extraction solvent and the remnant reaction product is essentially quantitatively extractable. However, the invention could be practiced in other ways, as, for example, by providing that the dipeptide reaction product be extractable, so that a labelled dipeptide could be measured after extraction.

Alternatively, the substrate could be solvent-extractable while the labelled product was not, so that the reaction could be measured by monitoring disappearance of substrate. Other embodiments within the scope of the present invention which foreseeably could be developed using presently known techniques include the provision of a radioactive label in a part of the substrate destined to become one of the enzymatic cleavage products and the provision of a substrate separable from its enzymatic cleavage products.

Non-radioactive substrates of the present invention may also be employed to measure ACE activity. For example, the extracted component could be capable of reacting with a reagent to produce a color or a fluorescence.

The preferred substrates of the present invention have the following properties:
 (a) capable of being bound to the enzyme to form a reversible enzyme-substrate complex with a sufficiently low dissociation constant to insure that the enzyme reaction occurs at a reasonable rate.
 (b) hydrolyzable by the enzyme, preferably having only one susceptible peptide bond.
 (c) contain radioactive label incorporated entirely on the N-terminal side of the susceptible peptide bond.
 (d) largely insoluble in the organic solvent used to extract the remnant product.
 (e) provide a remnant product which may be extracted into an organic solvent essentially quantitatively.

These criteria are satisfied by certain derivatives of tri- and tetrapeptides aving radioactively labeled aromatic substitutents at the terminal amino group. Three such substrates in the present invention are $^3$H-hippurylglycylglycine ($^3$H-HipGlyGly) and $^{125}$I-p-hydroxyphenylpropionylglycylglycylglycine ($^{125}$I-HPPGlyGlyGly) and $^3$H-benzoylprolylphenylalanylarginine ($^3$H-benzoylProPheArg).

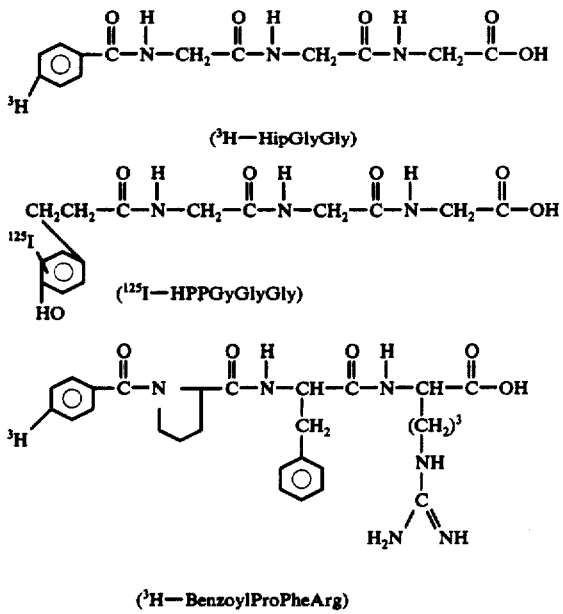

In principle, the invention encompasses any radioactively labelled peptide derivative satisfying the above-mentioned general criteria. Other amino acid sequences may be suitable. other radioisotopes, such as $^{35}$S, and $^{131}$I may be employed. The nature of the substituent on the terminal nitrogen may be varied within the scope of the invention as long as the above-mentioned criteria remain satisfied.

The method of assay employing the aforementioned substrates may in principle be applied in any biological material containing ACE including perfused tissue, tissue homogenates, extracts and the like. The method is especially suitable for the assay of ACE in samples of clinical material, serum, urine and the like. Detailed methods have been developed for analysis of serum. When scintillation counting is to be employed for measurement of radioactivity, it is necessary to obtain non-hemolyzed blood, because the presence of homoglobin in the serum reduces the efficiency of scintillation counting in a manner which is difficult to compensate for.

Reaction conditions optimal for carrying out an ACE catalyzed hydrolysis of a substrate of the present invention are the same as have been previously described for substrates known in the prior art. Detailed studies of optimal conditions using HipGlyGly as substrate have been reported by Dorer, et al. The pH optimum is approximately 8.0 although greater than 50% maximal activity is obtained in the pH range 7.0 - 9.0, in the pressence of 1M NaCl. When HipGlyGly or I-HPPGlyGlyGly are used as substrates, the enzyme requires chloride ions although this requirement is partially satisfied by providing a high ionic strength. The relationship between the chloride requirement and the ionic strength requirement has not been fully characterized. Buffer composition significantly affects enzyme activity. Phosphate is inhibitory. Hepes, bicine and barbital buffers are suitable for use but Hepes is preferred because it provides maximum activity. Preferred conditions of buffer composition, ionic strength, pH and temperature are described in Example 1. When the substrate is BenzoylProPheArg, chloride ions and high total ionic strength do not greatly affect the rate of the ACE catalyzed hydrolysis and may be omitted, optionally. The pH range for usable enzyme activity is from pH 6.5 to pH 8.7, with a broad plateau of maximal activity ranging from pH 7.2 to pH 8.5. Optimal substrate concentration depends upon the apparent Km, for the substrate compared with the Km's of possible competing substances in the sample. A sbstrate having a relatively low Km, such as $^3$H-benzoylProPheArg (Km 2 × $10^{-4}$M) could be suitably used at a concentration less than its Km. A substrate having a higher Km might better be used at a concentration greater than its Km. The preferred substrate concentration for a standard serum assay using $^3$H-HipGlyGly as substrate is 8 × $10^{-3}$ molar, approximately 1.3 times Km (see Example 1). $^3$H-HipGlyGly and $^{125}$I-HPPGlyGlyGly are preferred substrates for measuring ACE activity in serum because they are insensitive to serum carboxypeptidase, whigh might otherwise interfere with the reaction and give anomalous results. Because its Km is the lowest of any of the substrates of the present invention, $^3$H-benzoylProPheArg is the most preferred substrate for assays where ACE activity is low and maximum sensitivity is desired. In addition to being less sensitive to competitive inhibition, assays carried out with this substrate are potentially able to measure lower levels of ACE than the other substrates disclosed herein. Additionally, its partition behavior in an aprotic organic solvent is extremely favorable: only about 3% entered ethyl acetate in a preliminary extraction experiment. The remnant product Benzoylproline was about 90% extracted.

The effect of temperature on the ACE-catalyzed reaction is similar to enzyme catalyzed reactions in general. An approximately 2-fold decrease in reaction rate may be expected for every 10° C. decrease in temperature. An upper temperature limit is determined by the temperature of heat inactivation. In principle, the assay could be carried out at temperatures ranging approximately from 20° C – 50° C. An assay temperature of 37° C is preferred because this temperature duplicates physiological conditions and because data obtained at 37° C can be directly compared with data reported by other workers in the area.

The reaction may be terminated by any suitable means known in the art for terminating enzyme catalyzed reactions as long as such means does not interfere with the subsequent extraction of the remnant product. The method preferred herein, for terminating the reaction is the addition of a ten-fold excess volume of 0.1 M hydrochloric acid.

The remnant reaction product may be extracted from the reaction mixture by any aprotic organic solvent which affords a reasonably quantitative separation of product from substrate. The use of solvents which may interfere with the counting process is to be avoided. Ethyl acetate is preferred. Approximately 91% of $^3$H-Hippuric acid is extracted into ethyl acetate. Extraction may be carried out by any suitable means familiar to those skilled in the art, such as shaking, agitating, mixing and the like. Separation of the phases is conveniently accomplished by centrifugation. Centrifugation at 1000×G for 10 minutes is preferred, either at room temperature or in a refrigerated centrifuge. In some cases, an emulsion will form which can be separated by a longer centrifugation step.

A suitable aliquot of the organic phase is then removed for radioactivity counting. Radioactivity may be counted by any suitable means known in the art for obtaining quantitative results. Scintillation counting is preferred, however, other techniques such as planchet counting, strip scanning, autoradiography and the like may be employed. The choice of counting method will be dictated by the individual investigator's or clinician's needs and the available equipment.

Potential interfering factors are product inhibition and possible ACE inhibitors in serum. Product inhibition has been observed to occur in the standard assay (Example 1) when the product dipeptide GlyGly has accumulated to the extent that about 20% or more of the substrate has been hydrolyzed. With normal serum, this much hydrolysis does not occur in a standard 60 minute incubation. However, product inhibition has occasionally been observed with highly active sarcoid serum samples, resulting in erroneously low values. The errors can be corrected by repeating the assay using serum diluted two-fold or more over the standard dilution. (See Example 1). Possible interference by ACE inhibitors in serum can also be circumvented by employing a serum sample of higher dilution than the standard assay. As a general precaution, any sample displaying a higher than normal activity should be reassayed with a more dilute serum sample.

The practice of the invention will be further demonstrated by the examples.

EXAMPLE 1

The following sample illustrates the preferred assay method, the sensitivity of the assay and the Km for $^3$H-HipGlyGly. The reaction buffer contains 0.05 M Hepes, 0.1 M sodium chloride and 0.6 M sodium sulphate at pH 8.0. (Hepes is N-2-Hydroxyethyl piperazine N'-2-ethane sulfonic acid.) The substrate, $^3$H-HipGlyGly was dissolved in reaction buffer at a concentration of 16 mM and a specific radioactivity of about 0.15 millicuries/millimole. Serum was prepared from fresh whole blood by standard techniques. The addition of EDTA was avoided since EDTA is a potent inhibitor of ACE. Hemolyzed samples were not used in the assay. Serum samples could be stored at least for 1 week at 2° C to 8° C or for at least 8 weeks frozen, prior to assaying. For the assay, 50 μl. of serum was diluted with 200 μl. of reaction buffer. All the reactions were carried out in glass tubes due to the potentially destructive action of ethyl acetate on plastic.

The reaction mixture was composed of 50 μl. of diluted serum, an appropriate amount of substrate solution depending on the final substrate concentration desired, and reaction buffer sufficient to give a total reaction volume of 100 μl. All reaction tubes were incubated for 60 minutes at 37° C. Reactions were terminated by the addition of 1.0 ml. of 0.1N hydrochloric acid. The reaction mixture was then extracted with 1.0 ml. ethyl acetate, by rotary agitation for 4–5 seconds. The phases were separated by centrifugation at 1000 × G for 10 minutes. A 0.5 ml. sample of the ethyl acetate (upper) layer was removed and transferred to a scintillation vial containing 10 ml. scintillation fluid. (Riafluor, Trademark, New England Nuclear Corp., Boston, Mass.)

A control determination of background radioactivity was made using 50 μl. of reaction buffer instead of diluted serum in the reaction mixture. The purpose of this control was to determine the number of total counts attributable to background radiation, non-specific release of hippuric acid and the presence of unreacted substrate in the ethyl acetate phase. Less than 7% of the $^3$H-HipGly Gly entered the organic phase. Total radioactivity was determined by counting an amount of substrate equal to that used in the reaction mixture directly in the scintillation counter.

Reaction velocity, in terms of nanomoles of product formed per minute per ml of serum was calculated according to the following formula:

$$\text{nmoles/min/ml} = \frac{800 \text{ nmoles (cpm in sample} - \text{cpm in blank)}}{(\text{total cpm}) (60 \text{ min}) (0.01 \text{ ml})} \times 2$$

In this formula, "nmoles" means nanomoles, "min" means minutes, "ml" means milliliters and "cpm" means radioactivity counts per minute. The factor of 2 is a correction for the aliquot size. In the case where a significant fraction of substrate has been hydrolyzed, and the substrate is one which is more soluble in the organic phase, as for example, $^{125}$I-HPPGlyGlyGly, a modified formula is used to take account of the decreasing amount of substrate extracted as the reaction progresses:

$$\text{nmoles/min/ml} = 2 \times$$

-continued $$\frac{800 \text{ nmoles}(\text{cpm in sample} - \text{cpm in blank})\left(1 - \frac{\text{cpm in blank}}{\text{total cpm}}\right)}{(\text{total cpm}) (60 \text{ min}) (0.01 \text{ ml})}$$

The results are presented in the following table.

Table II

| μmoles/assay | [S]mM | $\frac{1}{[S]}$ | Velocity $\frac{\text{(nmoles)}}{\text{(min.ml)}}$ | $\frac{1}{V}$ |
|---|---|---|---|---|
| 0.909/0.1ml | 9.09 | 0.11 | 54.63 | 0.0183 |
| 0.727/0.1ml | 7.27 | 0.14 | 52.48 | 0.0191 |
| 0.545/0.1ml | 5.45 | 0.18 | 46.76 | 0.0214 |
| 0.364/0.1ml | 3.64 | 0.27 | 34.65 | 0.0289 |
| 0.1818/0.1ml | 1.82 | 0.55 | 19.83 | 0.0504 |
| 0.0909/0.1ml | .91 | 1.10 | 12.35 | 0.0810 |

Reciprocal values of initial substrate concentration and reaction velocity were calculated and graphed according to the method of Lineweaver and Burke, as shown in FIG. 1. A straight line was obtained, which intercepted the ordinate at a value equal to the reciprocal of the maximum velocity of the enzyme reaction and intercepted the abcissa at a value equal to the negative reciprocal of the apparent Michaelis constant. The Km calculated by this method for the substrate HipGlyGly was $6.25 \times 10^{-3}$M. This value is in general agreement with the Km reported by Dorer, et al., cited above, who reported a Km for HipGlyGly of $2.6 \times 10^{31 \, 3}$M under similar reaction conditions using enzyme derived from hog lung. It can be seen that reaction velocities as low as 12 nanomoles of substrate hydrolyzed per minute per ml. of serum can readily be measured.

EXAMPLE 2

Further demonstration that the activity observed with the present assay method in human serum is identical to ACE was provided by observing the effects of known specific inhibitors of ACE. In this series of reactions, the procedure described in Ex. 1 was followed except that the substrate concentration was 8mM throughout and specific inhibitor substances were added at the indicated final concentration. Bradykinin, angiotensin I, $BPP_{5a}$ and EDTA have been described hereinabove. $BPP_{9a}$ (SQ20881) is a nonapeptide from snake venom having the sequence <GluTryProArg-ProGlnIleProPro. The results are shown in Table III.

TABLE III

INHIBITION OF SERUM ANGIOTENSIN
CONVERTING ENZYME BY VARIOUS COMPOUNDS*

| Compound | Final Concentration(M) | Δ CPM (counts per minute)** | ACE Activity as % of control |
|---|---|---|---|
| Control |  | 3800 | 100 |
| Bradykinin | $2.7 \times 10^{-7}$ | 3267 | 86 |
| Bradykinin | $2.7 \times 10^{-6}$ | 3165 | 83 |
| Bradykinin | $2.7 \times 10^{-5}$ | 1553 | 41 |
| Angiotensin I | $9 \times 10^{-7}$ | 3057 | 81 |
| Angiotensin I | $9 \times 10^{-6}$ | 2557 | 67 |
| Angiotensin I | $4.5 \times 10^{-5}$ | 1278 | 34 |
| $BPP_{5a}$ (SQ20475) | $9 \times 10^{-8}$ | 3519 | 93 |
| $BPP_{5a}$ (SQ20475) | $9 \times 10^{-7}$ | 2440 | 64 |
| $BPP_{5a}$ (SQ20475) | $4.5 \times 10^{-6}$ | 830 | 22 |
| $BPP_{9a}$ (SQ20881) | $2.8 \times 10^{-9}$ | 2200 | 58 |
| $BPP_{9a}$ (SQ20881) | $9 \times 10^{-8}$ | 1410 | 37 |
| EDTA | $9 \times 10^{-4}$ | 1178 | 31 |

*Standard assay conditions as described in Example 1 were used.
**ΔCPM = (CPM of compound - CPM of Blank)

The results are consistent with prior findings of specific inhibition of ACE by the compounds of Table III, and thereby further demonstrate that the activity measured by the method of the present invention is ACE.

Parenthetically, it may be noted that since angiotensin I and bradykinin are considered to be the natural substrates for ACE, they behave as competitive inhibitors of the ACE catalyzed hydrolysis of the substrate of the present invention.

EXAMPLE 3

This experiment demonstrates the precision of the assay method of the present invention. Replicate serum samples from normal individuals having ACE levels in the low and mid-range, from a patient with active sarcoidosis and from guinea pig serum were made using the standard assay procedure of Example 1. With 8 mM substrate the results of replications within the same day and from day to day are given in Table IV.

TABLE IV

PRECISION DATA FOR ANGIOTENSIN CONVERTING ENZYME ASSAY

|  | n | Mean nanomoles/min/ml | 1 Standard Deviation | % Coefficient of Variation |
|---|---|---|---|---|
| Within Day |  |  |  |  |
| Guinea Pig Control | 19 | 1448 | 60 | 4.2 |
| Low Normal | 20 | 48.3 | 4.9 | 10.3 |
| Normal | 20 | 86.2 | 3.7 | 4.3 |
| Day to Day |  |  |  |  |
| Guinea Pig Control | 12 | 1552 | 74.8 | 4.8 |
| Low Normal | 12 | 45 | 3.6 | 7.9 |
| Positive Sarcoid | 12 | 184 | 6.6 | 3.6 |
| Blank | 20 | (5.5) | .33 | 5.9 |

The observed variability lies within the range expected for microchemical analyses involving volumetric transfers with pipets. The results corroborate published reports that serum ACE levels of patients with active sarcoidosis are higher than normal levels. Normal values for ACE activity in adults between the ages of 18 to 55 range from 85 units per ml. to 120 units per ml. However, such normal values may change with age.

EXAMPLE 4

The synthesis of $^{125}$I-HPPGlyGlyGly was carried out by mixing 100 μl of a solution containing 1.892 mg GlyGlyGly and 1.682 mg sodium bicarbonate in water with a solution containing $2.723 \times 10^7$ counts per minute (counted at 30% counting efficiency) Bolton-Hunter reagent ($^{125}$Iodo-p-hydroxyphenylpropionyl-N-hydroxysuccinimide from New England Nuclear Corp., Boston, Mass.) in 100 μl tetrahydrofuran. The mixture was incubated overnight at refrigerator temperature (about 4° C). A small amount of benzene was then added sufficient to make the mixture homogeneous. The mixture was separated by thin layer chromatography using a solvent mixture of 9 parts (by volume) benzene, 1 part water and 9 parts acetic acid. The radioactivity was found in a large spot at the solvent front, representing the radioactive reactant and a probable degradation product thereof, and a smaller spot near the middle of the chromatogram representing the product, $^{125}$I-HPPGlyGlyGly. The product spot was eluted from the chromatogram with methanol and stored in the same solvent. Although the radioactive product was believed to be predominantly monosubstituted with respect to iodine, it is possible that about 2% - 3% of the diiodo derivative could be present also.

EXAMPLE 5

The following experiment demonstrates the feasibility of using $^{125}$I-HPP-GlyGlyGly as an ACE substrate in the method of present invention. The standard assay conditions as described in Example 1 were employed except that the source of ACE was guinea pig serum and the amount of substrate added was that amount needed to give 101,436 total counts per minute. In terms of mass, this amount is believed to be well below the Km for the substrate. Samples were incubated for 15 minutes, 30 minutes and 60 minutes, and an unreacted sample (0 time) was used to determine the amount of substrate extracted into ethyl acetate. Net counts were calculated on the basis that 27.2% of the unhydrolyzed substrate was contained in the ethyl acetate phase. Results are shown in Table V.

Table V

| Incubation Time (min). | cpm in Ethyl Acetate phase | Net cpm in product |
|---|---|---|
| 0 | 27,205 | 0 |
| 15 | 40,000 | 17,808 |
| 30 | 59,182 | 43,804 |
| 60 | 69,577 | 58,044 |

It can be seen that despite an appreciable background caused by the fact that 27.2% of the unhydrolyzed substrate was extracted by ethyl acetate, there is appreciable conversion of the substrate in a 60 minute incubation, under standard ACE reaction conditions.

EXAMPLE 6

Iodo-BenzoylProPheArg was prepared by first mixing 390 mg prolylphenylalanylnitroarginine benzyl ester together with 98 mg 1-hydroxybenzotriazole in dimethyl formamide and neutralizing the mixture with N-ethyl morpholine at 0° C. A cool solution of p-iodobenzoic acid N-succinimidyl ester (200 mg) was added. The reactants were stirred for 1 hour in an ice bath, then transferred to room temperature for stirring overnight. The solvent was then removed under reduced pressure and the residue extracted with ethyl acetate. The ethyl acetate phase was subjected to a series of washes in the sequence: water, 0.2N HCl, saturated NaCl, saturated NaHCO$_3$, saturated NaCl. The ethyl acetate solution was then dried over anhydrous MgSO$_4$. A gum-like material remained after solvent removal, which was reactive with o-tolidine/Cl$_2$ reagent, non-reactive with ninhydrin and which migrated as a single spot on paper electrophoresis at pH 2.0. These properties indicated that the material was substantially the expected product, p-Iodobenzoylprolylphenylalanylnitroarginine benzyl ester.

The aforementioned product was then treated with HF in the presence of anisole to remove the protecting groups. The resultant peptide p-Iodobenzoylprolylphenylalanylarginine was purified by chromatography on Sephadex G-10 (Sephadex, Trademark, Pharmacia, Uppsala, Sweden), eluted with 15% (v/v) aqueous acetic acid. The peptide peak was detected by monitoring absorbance at 280 nm. Homogeneity was confirmed by paper electrophoresis at pH 2.0 and pH 5.0, and by thin layer chromatography in seven different solvent systems.

The peptide p-Iodobenzoylpropylphenylalanylarginine was submitted to New England Nuclear Corp., Boston, Mass. for custom tritiation by a process of catalytic dehydrohalogenation in the presence of tritium gas.

The radioactive product was characterized by chromatography on Bio-Gel P2 (Bio-Gel, Trademark, BioRad Laboratories, Richmond, California), paper electrophoresis and thin layer chromatography. A Biogel P2 column, having 110 ml column volume and 50 ml to 55 ml void volume was loaded with a sample of $^3$H-BenzoylProPheArg and eluted with a pyridine acetic acid buffer, 0.1M, pH 5.0. Equal fractions of 2 ml volume were collected. A peak of radioactivity at tube 43 was observed, corresponding to an elution volume of 86 ml. No other radioactive peaks were observed.

A sample of $^3$H-BenzoylProPheArg was chromatographed on a thin layer silica gel plate in a solvent system composed of 150 parts by volume n-butanol, 26 parts acetic acid and 24 parts water. $^3$H-BenzoylProPheArg had an Rf of 0.32. A comparison sample of benzoylproline had an Rf of 0.55 in the same solvent system.

Paper electrophoresis was carried out on Whatman 3 MM paper at 1100 volts and 10–20 milliamps per hour at pH 2.0 and pH 5.0. The pH 2.0 buffer contained 100 ml diethylene glycol, 120 ml. acetic acid, 20 ml formic acid and 760 ml water. The pH 5.0 buffer contained 27.8 ml glacial acetic acid, 32.2 ml pyridine and sufficient water to make 4 l. final volume. At pH 2.0 $^3$H-BenzoylProPheArg migrated 6.6 centimeters relative to arginine which traveled 18 centimeters. At pH 5.0 $^3$H-BenzoylProPheArg migrated 2.5 centimeters compared to 16.5 cm for arginine.

Hydrolysis of 1.25 mm μM $^3$H-BenzoylProPheArg using the standard reaction procedure of Example 1 with normal human serum as the ACE source was measured in the absence and in the presence of competing substrates and an inhibitor. The results are shown in Table VI.

TABLE VI

HYDROLYSIS OF $^3$H-BENZOYLProPheArg BY NORMAL HUMAN SERUM: EFFECT OF VARIOUS COMPOUNDS

| Compound | Final Concentration (M) | ACE Activity As % of Control |
|---|---|---|
| Control |  | 100 |
| EDTA | $1 \times 10^{-3}$ | 23 |
| BPP$_{9a}$ (SQ20881) | $3.3 \times 10^{-5}$ | 28 |
| Bradykinin | $8.2 \times 10^{-5}$ | 21 |
| Angiotensin I | $7.1 \times 10^{-5}$ | 27 |

GENERAL CONCLUDING REMARKS

The substrates of the invention described herein make it possible to carry out assays for angiotensin converting enzyme activity with greater speed and convenience than has been heretofore possible. The ability to carry out such assays is of great clinical utility as well as research interest. Two of the substrates of the present invention are novel compounds.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A composition of matter consisting essentially of

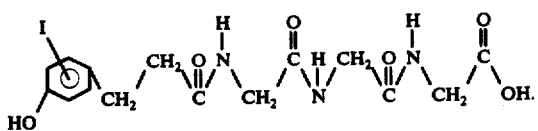

2. The composition of claim 1 wherein at least a portion of the Iodo-p-hydroxyphenylpropionyl moiety contains a radioisotope.

3. The composition of claim 1 wherein at least a portion of the iodine atoms is replaced by a radioisotope of iodine.

4. A composition of matter consisting essentially of

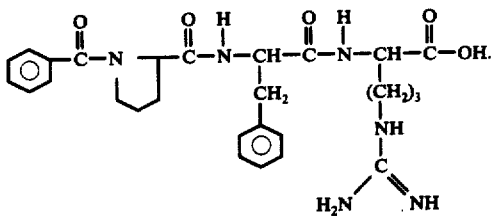

5. The composition of claim 4 wherein at least a portion of the benzoyl moiety attached to proline contains a radioisotope.

6. The composition of claim 4 wherein at least a portion of the hydrogen of the benzoyl moiety attached to proline is replace by tritium.

* * * * *